United States Patent [19]

Lawrence et al.

[11] Patent Number: 5,922,913
[45] Date of Patent: Jul. 13, 1999

[54] PROCESS FOR NITRATING AROMATIC AMINES

[75] Inventors: Lowell J. Lawrence; Stefan Kwiatkowski, both of Lexington, Ky.; Paul D. Smith, Seabrook, Tex.

[73] Assignee: SRM Chemical, Ltd., Co., League City, Tex.

[21] Appl. No.: 09/187,949

[22] Filed: Nov. 6, 1998

[51] Int. Cl.[6] .................................................. C07C 209/00
[52] U.S. Cl. ........................................... 564/411; 564/441
[58] Field of Search ...................... 564/411, 441

[56] References Cited

U.S. PATENT DOCUMENTS

| | | | |
|---|---|---|---|
| 3,726,923 | 4/1973 | Foster et al. | 260/577 |
| 3,929,916 | 12/1975 | Levy et al. | 260/645 |
| 3,929,917 | 12/1975 | Rauch et al. | 260/645 |
| 3,976,704 | 8/1976 | Vaughan | 260/645 |
| 4,101,582 | 7/1978 | Lutz et al. | 260/574 |
| 4,112,005 | 9/1978 | Thiem et al. | 260/645 |
| 4,136,117 | 1/1979 | Diehl et al. | 260/577 |
| 4,174,400 | 11/1979 | Mrozik | 424/273 |
| 4,261,926 | 4/1981 | Row et al. | 564/385 |
| 4,609,759 | 9/1986 | Carr | 564/395 |
| 5,369,086 | 11/1994 | James et al. | 504/253 |
| 5,696,305 | 12/1997 | Klingler et al. | 568/934 |
| 5,705,698 | 1/1998 | Lawrence et al. | 564/419 |

FOREIGN PATENT DOCUMENTS 0847984   6/1998   European Pat. Off. .

OTHER PUBLICATIONS

Kobe et al., *Industrial and Engineering Chemistry* 44:1398–1401 (Jun. 1952).
Glazer et al., *Nitration of Aromatic Quinines*, pp. 2657–2677 (1950).

*Primary Examiner*—Paul J. Killos
*Attorney, Agent, or Firm*—Arnold White & Durkee

[57] ABSTRACT

Disclosed is a process of nitrating or dinitrating an aromatic amine compound that involves reacting the aromatic amine and nitric acid in the presence of acetic acid such that the molar ratio of the aromatic amine compound to acetic acid is from about 1:2 to about 1:16, and the molar ratio of nitric acid to the aromatic amine is between about 1.0 to about 1.5 times the nitric acid needed to complete the reaction. More particularly, the invention is a process of forming Pendimethalin, N-(1-ethylpropyl)-2,6-dinitro-3,4-xylidine, from N-(1-ethylpropyl)-3,4-xylidine (4-NAX) that involves reacting 4-NAX and nitric acid in the presence of acetic acid such that the molar ratio of nitric to the 4-NAX is between about 2:1 and about 3:1, preferably between about 2:1 and about 2.6:1, and such that the molar ratio of 4-NAX to acetic acid is between about 1:2 to about 1:16, preferably between about 1:4 and about 1:8.

24 Claims, No Drawings

PROCESS FOR NITRATING AROMATIC AMINES

FIELD OF THE INVENTION

The invention relates to a process of nitrating aromatic amines. In particular, this invention relates to a process for manufacturing Pendimethalin by nitrating N-(1-ethylpropyl)-3,4-xylidine to Pendimethalin, also known as N-(1-ethylpropyl)-2,6-dinitro-3,4-xylidine.

BACKGROUND OF THE INVENTION

Aromatic amine compounds, particularly substituted aniline compounds, have been dinitrated to form dinitroaniline compounds which are useful as herbicides. The desired nitration takes place in the aromatic ring of the amine. It is known that nitric acid is a nitrating agent useful to nitrate an organic compound.

One problem with nitrating an aromatic amine is the protection of the amino group because nitration of primary aromatic amines yields unstable products. In the case of secondary aromatic amines, it is believed that the intermediate N-nitro and N-nitroso compounds are rearranged in acidic conditions to ring nitrated products. Since the amine compounds are susceptible to oxidation, it is often necessary to protect the amine group during nitration, for instance by converting the amine to its acyl derivative.

A second problem is that the nitration process can be slowed by the accumulation of water. The nitration process is usually carried out with nitric acid as the nitrating agent. Water is a byproduct, and the presence of water interferes with the nitration process. It is known in the industry to use a large excess of a nitric and sulfuric acid mixture, as the nitrating agent to minimize the adverse effects of water accumulation. This large excess is costly, and the partially depleted nitric acid-containing mixture is waste. The prior art also apparently addresses this problem by adding a water-immiscible solvent to allow partition of water formed during nitration from the reaction mixture into the aqueous acid phase. However, separation of reactants into two phases can result in operational problems.

One method of minimizing water interference is to add a water scavenger to the nitration mixture. U.S. Pat. No. 4,101,582 describes nitrating 4-chloro-o-xylene with fuming sulfuric acid and fuming nitric acid at a temperature between 10° C. and 60° C. This minimizes the water buildup by the reaction of water with excess $SO_3$ in the fuming acid. A major disadvantage to this method is the formation on large quantities of waste acid that pose potential environmental problems.

A second method of dealing with water is to nitrate in multiple steps, wherein weaker nitric acid is used to protonate the aromatic amine and then stronger nitric acid is used to nitrate the salt of the aromatic amine. For example, U.S. Reissue Pat. No. 33,168 describes a process to dinitrate a substituted aniline compound in several discrete steps, the first of which is reacting the substituted aniline compound with dilute, i.e., 20%–50%, nitric acid in the presence of a liquid, water-immiscible organic solvent to form a partially nitrated salt. The diluted nitric acid from the first step is then removed and concentrated nitric acid is added to effect dinitration. The mononitrated product is then reacted with the concentrated nitric acid to form a dinitro product. Finally, the water-immiscible organic solvent, i.e., chlorinated hydrocarbons, is removed by vacuum. This process requires multiple discrete steps and separations and results in the contamination of waste streams by chlorinated hydrocarbons.

The prior art also describes nitration methods that require protection of the amino group, i.e. by acylation prior to nitration. The amino group may be protected by reacting the aromatic amine with acetic acid or acetic anhydride, performing the nitrating step, and then removing the acetyl group. For instance, U.S. Pat. No. 5,369,086 describes a process of producing 2-nitro-4-methyl-5-methoxyacetanilide by reacting 4-methyl-3-methoxyaniline with acetic acid and acetic anhydride. Then, nitric acid is added to the reaction mixture to give 2-nitro-4-methyl-5-methoxyacetanilide. The process uses approximately four times the stoichiometric quantity of nitric acid. Finally, this product is reacted with concentrated hydrochloric acid at reflux temperature to remove the acetyl group, giving 2-nitro-4-methyl-5-methoxyaniline. This is a costly additional step, and it creates waste.

The prior art has also described processes that do not protect the amine. For example, U.S. Pat. No. 3,726,923 describes a process of nitrating an aromatic amine to form a dinitro product in a single step. The reaction is carried out with a water-and acid-immiscible solvent that contains the organic reactant. Similarly, U.S. Pat. No. 4,136,117 describes a high yield process of nitrating N-alkylated secondary anilines in the 2,6 positions without protection of the amino group. The nitrating agent is a mixture of water, nitric acid, and sulfuric acid falling within certain concentration ranges. The N-alkyl-aniline is dissolved in an inert water-immiscible solvent, such as ethylene dichloride or other chlorinated hydrocarbon.

The above described methods generally produce substantial quantities of N-nitroso compounds, in part because large excesses of nitric acid are utilized. They also produce waste, including large quantities of waste acid and organic solvent waste.

What is needed is a process for dinitrating aromatic amine compounds wherein the reaction takes place in a single phase, and wherein large excesses of nitric acid are not required, and wherein sulfuric acid is not required, and wherein waste streams are not contaminated with chlorinated hydrocarbons and wherein the reaction is completed in a single step. What is also needed is a process wherein the generation of N-nitroso compounds is minimized.

SUMMARY OF THE INVENTION

The invention is a process of nitrating aromatic amines by reacting the aromatic amine and nitric acid in the presence of acetic acid such that the molar ratio of nitric acid to the aromatic amine compound is in the range of approximately 1.0 to about 1.5 times the nitric acid needed to complete the reaction, and such that the molar ratio of the aromatic amine to acetic acid is in the range of approximately 1:2 to 1:16.

More particularly, the invention is a process of dinitrating aromatic amines by reacting the aromatic amine and nitric acid in the presence of acetic acid such that the molar ratio of nitric acid to the aromatic amine compound is in the range of approximately 2:1 to 3:1 and such that the molar ratio of the aromatic amine to acetic acid is in the range of approximately 1:2 to 1:16.

Even more particularly, the invention is a process of manufacturing Pendimethalin, N-(1-ethylpropyl)-2,6-dinitro-3,4-xylidine, from N-(1-ethylpropyl)-3,4-xylidine (4-NAX) that involves mixing 4-NAX and nitric acid in the presence of acetic acid such that the molar ratio of nitric acid to the 4-NAX between about 2:1 to about 3:1 and such that the molar ratio of 4-NAX to acetic acid is between about 1:2 to about 1:16.

DETAILED DESCRIPTION OF THE INVENTION

The invention is a process for nitrating an aromatic amine in a single homogenous phase comprising nitric acid and acetic acid. More particularly, the invention is a process for dinitrating an aromatic amine in a single homogenous phase comprising nitric acid and acetic acid.

The nitric acid feedstock should be concentrated, i.e., above 80% by weight on a nitric acid/water basis. It is preferred that the concentration of nitric acid in the nitric acid feedstock be greater than about 90%, more preferably greater than about 95%, and most preferably greater than about 97% by weight on a nitric acid/water basis.

The acetic acid solvent should be glacial acetic acid. Preferably, the concentration of acetic acid in the glacial acetic acid should be greater than about 95%, more preferably greater than about 98%, by weight on an acetic acid/water basis. Mixtures of acetic acid and acetic anhydride are also suitable for use in the present invention.

The aromatic amine can be any aromatic amine suitable for nitrating on the aromatic ring. The particular utility for manufacturing dinitroaniline herbicides requires that the aromatic amine be a ring and/or N-substituted aniline, for example N-alkyl-3,4-xylidine. The particular utility for manufacturing Pendimethalin, also known as N-(1-ethylpropyl)-2,6-dinitro-3,4-xylidine, requires that the aromatic amine compound be N-(1-ethylpropyl)-3,4-xylidine (4-NAX). The chemical structures of 4-NAX, Pendimethalin, and the undesirable byproduct N-nitroso-Pendimethalin are shown below, where R is 1-ethylpropyl.

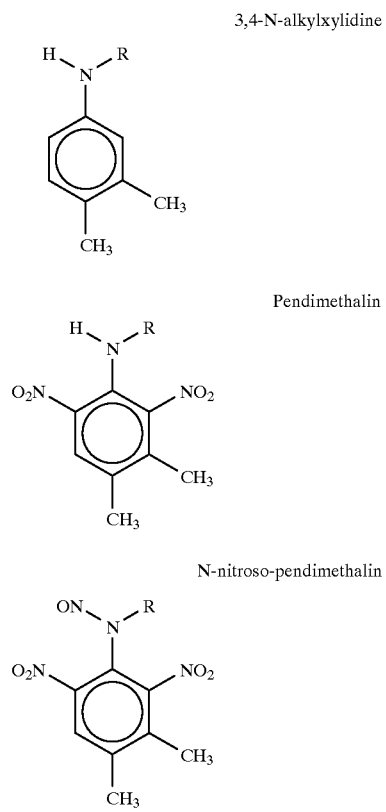

It is preferred that the quantity of feedstocks, particularly acetic acid, is such that the resulting composition is a homogenous liquid. The molar ratio of the aromatic amine, for example 4-NAX, to acetic acid prior to reacting should range from about 1:2 to about 1:16, preferably from about 1:4 to about 1:8, more preferably from about 1:5 to about 1:7.

The quantity of nitric acid should be near or above the stoichiometric quantity required, i.e., between about 1.0 to about 1.5 times the nitric acid needed to complete the desired reaction. In the case of dinitrating an aromatic amine compound, the molar ratio of the aromatic amine compound to nitric acid prior to reacting should range from about 1.0:2.0 to about 1.0:3.0, preferably from about 1.0:2.0 to about 1.0:2.6, more preferably from about 1.0:2.0 to about 1.0:2.4.

It is often desirable to have the aromatic amine dissolved in at least a portion of the acetic acid before adding any nitric acid. That is, one mole of the aromatic amine, i.e., 4-NAX, can be mixed in about four moles of acetic acid. Then, two moles of nitric acid and optionally an additional one to three moles of acetic acid can be mixed together, and then this mixture of acids can be added to the acetic acid-aromatic amine solution. This ensures that the reactants and the reaction product will remain in a single homogenous phase.

Depending on the amine characteristics, the reaction may require heating. The reaction time will vary with the particular aromatic amine compound to be nitrated as well as the mixture composition and the temperature.

For the dinitration of N-alkyl-3,4-xylidines, particularly the dinitration of 4-NAX to Pendimethalin, the reaction is best performed at a temperature between about 40° C. to about 80° C., preferably between about 50° C. to about 70° C., and more preferably between about 55° C. to about 65° C. It is preferred that the composition, after the complete addition of nitric acid, be held at the reaction temperature for between about 10 minutes to about 12 hours, more preferably from about 30 minutes to about 4 hours, and most preferably from about 1 hour to about 3 hours. The optimum time will depend on the reaction temperature. This insures that the reaction is complete within normal processing constraints.

It is then often advantageous to separate the acetic acid and other volatiles, i.e., water, from the reacted composition. For Pendimethalin, the acetic acid and other volatiles can be removed by vacuum, with agitation or other method of promoting evaporation. It is preferred that the acetic acid and other volatiles be removed from the reacted composition by applying a vacuum. The degree of vacuum and the time required will depend on the composition temperature and the agitation. For typical reactors containing Pendimethalin, a vacuum between about 5 mm of mercury and about 100 mm of mercury, preferably between about 10 mm of mercury and 20 mm of mercury, is preferred at ambient temperature, i.e., about 23° C.

The recovered acetic acid is advantageously recycled.

EXAMPLE 1

In a reactor, 0.235 moles of 4-NAX and 1.04 moles of glacial acetic acid were mixed and the mixture was heated to 60° C. Then, a mixture of 0.562 moles nitric acid (as 98% pure nitric acid in water) and 0.517 moles glacial acetic acid were added dropwise with mixing and cooling to keep the temperature at about 60° C. The mixture was then kept at about 60° C. for an additional 2.5 hours. The mixture was then cooled to about ambient temperature, and a vacuum of 15 mm of mercury was drawn until the water and acetic acid were removed from the mixture.

This process generated approximately 85 weight percent Pendimethalin and 15 weight percent N-nitroso- Pendimethalin at essentially quantitative yields as determined by High Pressure Liquid Chromatography.

What is claimed is:

1. A process of nitrating an aromatic amine compound comprising:
   a) providing the amine and between about 1.0 to about 1.5 times the nitric acid needed to complete the reaction;
   b) mixing the aromatic amine compound and the nitric acid in the presence of acetic acid such that the molar ratio of the aromatic amine compound to acetic acid is from about 1:2 to about 1:16, and;
   c) reacting said mixture to form a nitrated aromatic amine compound.

2. A process of dinitrating an aromatic amine compound comprising:
   a) mixing the aromatic amine compound and nitric acid in the presence of acetic acid such that the molar ratio of nitric acid to the aromatic amine compound is from about 2:1 to about 3:1 and such that the molar ratio of the aromatic amine compound to acetic acid is from about 1:2 to about 1:16; and
   b) reacting said mixture to form a dinitrated aromatic amine compound.

3. The process of claim 2 wherein the nitric acid contains less than about 10% by weight water.

4. The process of claim 2 wherein the nitric acid contains less than about 5% by weight water.

5. The process of claim 2 wherein the nitric acid contains less than about 3% by weight water.

6. The process of claim 2 wherein the acetic acid contains less than about 5% by weight water.

7. The process of claim 2 wherein the acetic acid contains less than about 2% by weight water.

8. The process of claim 2 wherein the acetic acid comprises acetic acid and acetic anhydride.

9. The process of claim 2 wherein the aromatic amine compound comprises N-alkyl-3,4-xylidine.

10. The process of claim 2 wherein the aromatic amine compound comprises N-(1-ethylpropyl)-3,4-xylidine.

11. The process of claim 2 wherein the molar ratio of the aromatic amine compound to acetic acid is from about 1:4 to about 1:8.

12. The process of claim 2 wherein the molar ratio of the aromatic amine compound to acetic acid is from about 1:5 to about 1:7.

13. The process of claim 2 wherein the molar ratio of nitric acid to the aromatic amine compound is from about 2:1 to about 2.6:1.

14. The process of claim 2 wherein the molar ratio of nitric acid to the aromatic amine compound is from about 2:1 to about 2.4:1.

15. The process of claim 2 further comprising the step of mixing the aromatic amine compound and at least a fraction of the acetic acid prior to mixing nitric acid and the remaining acetic acid.

16. The process of claim 9 further comprising heating the mixture to between about 40° C. to about 80° C.

17. The process of claim 9 further comprising heating the mixture to between about 50° C. to about 70° C.

18. The process of claim 9 further comprising heating the mixture to between about 55° C. to about 65° C.

19. The process of claim 9 further comprising holding the mixture at temperature for between about 10 minutes to about 12 hours.

20. The process of claim 9 further comprising holding the mixture at temperature for between 30 minutes to about 4 hours.

21. The process of claim 9 further comprising holding the mixture at temperature for between about 1 hour to about 3 hours.

22. The process of claim 2 further comprising separating acetic acid and other volatiles from the reacted mixture.

23. The process of claim 22 further comprising separating acetic acid and other volatiles from the reacted mixture by applying a vacuum of between about 5 mm of mercury and about 100 mm of mercury.

24. The process of claim 23 wherein the vacuum is between about 10 mm of mercury and 20 mm of mercury.

* * * * *